United States Patent [19] [11] 4,316,894
Omoto et al. [45] Feb. 23, 1982

[54] ANTIBIOTIC SF-1130-$X_3$ SUBSTANCE AND PRODUCTION AND USE THEREOF

[75] Inventors: Shoji Omoto, Tokyo; Jiro Itoh, Yokohama; Tomizo Niwa, Yokohama; Takashi Shomura, Yokohama; Tetsutaro Niizato, Kawasaki; Shigeharu Inouye, Yokohama, all of Japan

[73] Assignee: Meiji Seika Kaisha, Ltd., Tokyo, Japan

[21] Appl. No.: 185,592

[22] Filed: Sep. 9, 1980

[30] Foreign Application Priority Data

Sep. 19, 1979 [JP] Japan ............................... 54-119324

[51] Int. Cl.³ ................. A61K 35/00; A61K 31/70; A61K 31/71
[52] U.S. Cl. .................................. 424/116; 424/180; 424/181; 435/169; 536/18
[58] Field of Search .................. 424/116, 180, 181; 435/169; 536/18

[56] References Cited

U.S. PATENT DOCUMENTS 4,065,557 12/1977 Frommer et al. .................. 536/18
4,160,026 7/1979 Iwamatsu et al. ................. 424/116
4,175,123 11/1979 Junge et al. ....................... 536/18

Primary Examiner—Jerome D. Goldberg
Attorney, Agent, or Firm—Larson and Taylor

[57] ABSTRACT

A new antibiotic SF-1130-$x_3$ substance is produced by cultivating a microorganism Streptomyces myxogenes SF-1130 (deposited under FERM-P. 676 and ATCC 31305) in a liquid culture medium under aerobic conditions, and this antibiotic may be isolated from the fermentation broth of said microorganism and is useful as an inhibitor to $\alpha$-glucosidase and saccharase. Besides, this antibiotic, when orally given, is useful as a drug for suppressing an elevation in the level of blood sugar in living animals which have taken starch and/or sugars.

3 Claims, 3 Drawing Figures

ANTIBIOTIC SF-1130-X₃ SUBSTANCE AND PRODUCTION AND USE THEREOF

SUMMARY OF THE INVENTION

This invention relates to a new antibiotic designated as SF-1130-x₃ substance which is useful as an agent for inhibiting the enzymatic activity of glucosidase. This invention also relates to a process for the fermantative production of the new antibiotic, SF-1130-x₃ substance by incubating a strain of the genus Streptomyces followed by isolating the resultant antibiotic from the fermentation broth. This invention further relates to various uses of the SF-1130-x₃ substance as an inhibitor to α-glucosidase and to saccharase, and also as a drug for suppressing an elevation in the level of blood sugar in living animals, including men, which have taken starch and/or sugars.

BACKGROUND OF THE INVENTION

A number of useful substances are produced in and isolated from the culture broth of various strains of the genus Streptomyces. It is known that *Streptomyces myxogenes* SF-1130 (identified as FERM-P. 676 or ATCC 31305) produces an antibiotic called SF-1130 substance (see Japanese Patent Publication No. 30393/73). We, the present inventors, already found that the further antibiotic substances active against gram-negative bacteria are produced in the fermentation broth of the microorganism *Streptomyces myxogenes* SF-1130, and we succeeded in isolating these active substances from the broth and have designated them as SF-1130-x₁ substance and SF-1130-x₂ substance, respectively, as disclosed in the specification of Japanese Patent Application Pre-publication "Kokai" No. 26398/78 or U.S. Pat. No. 4,160,026.

We have made further research on the crude product containing the SF-1130-x₁ and -x₂ substances as obtained from the culture broth of *Streptomyces myxogenes* SF-1130, and we have now found that the crude product contains a new third ingredient which was not discovered before but exhibits a very weakly antibacterial activity, in addition to the SF-1130-x₁ substance and the SF-1130-x₂ substance. We have now succeeded in isolating this third component from the crude product and have designated this as SF-1130-x₃ substance. We have further noticed that the SF-1130-x₃ substance (hereinafter sometimes abbreviated as the compound of this invention) is an oligosaccharide of weakly basic nature having the physico-chemical properties as mentioned hereinafter which is the novel substance distinct from known closely related species of antibiotics, and that the compound of this invention is highly active to suppress the enzymatic activity of glucosidase.

An object of this invention is to provide a new antibiotic designated as SF-1130-x₃ substance which is useful as an agent for inhibiting the enzymatic activity of glucosidase and as a drug for suppressing an increase in the level of blood sugar in living animals and men which have taken starch and/or sugars. The other object of this invention is to provide a process of producing such a useful substance. Another objects will be clear from the following descriptions.

DETAILED DESCRIPTION OF THE INVENTION

According to a first aspect of this invention, therefore, there is provided SF-1130-x₃ substance which is an oligosaccharide of weakly basic nature in the form of colorless powder, which is soluble in water and dimethylsulfoxide, less soluble in methanol and ethanol but insoluble in acetone, ethyl acetate, chloroform and benzene and which shows positive reaction with silver nitrate-sodium hydroxide, red tetrazolium, anthrone and Greig-Leaback reagents, respectively; the SF-1130-x₃ substance being further characterized by:

(a) having a melting point of 183° C. (with decomposition) and a specific optical rotation $[\alpha]_D^{23} + 154°$ (c 1, in water);

(b) exhibiting an elemental analysis: C 43.31%, H 5.88%, N 1.71% and O 49.10% (balance);

(c) having no characteristic absorption peak in ultraviolet spectrum (in water containing 100 μg/ml of a pure sample of the SF-1130-x₃ substance);

(d) having an infrared absorption spectrum pelleted in potassium bromide corresponding to that shown in FIG. 1 of the attached drawings;

(e) having a proton nuclear magnetic resonance absorption spectrum in deuterium oxide corresponding to that shown in FIG. 2 of the attached drawings;

(f) having a carbon nuclear magnetic resonance absorption spectrum in deuterium oxide corresponding to that shown in FIG. 3 of the attached drawings; and (g) giving a single spot at $R_{raffinose} = 0.64$ in a paper chromatography by the descending method developed with ethyl acetate-pyridine-water (10:4:3 by volume) as the developing solvent and at $R_{raffinose} = 0.62$ in the same paper chromatography by the descending method with n-butanol-pyridine-acetic acid-water (6:4:1:3 by volume) as the developing solvent when the $R_{raffinose}$ values are calculated as assumed that raffinose gives a single spot at Rf = 1.00 in the same paper chromatography.

According to a second aspect of this invention, there is provided a process for the production of the new antibiotic, SF-1130-x₃ substance, which comprises cultivating a strain of the genus Streptomyces capable of producing SF-1130-x₃ substance in an aqueous liquid culture medium containing assimilable carbon and nitrogen sources under aerobic conditions for a period of time sufficient to produce and accumulate the SF-1130-x₃ substance in the culture, and then recovering the SF-1130-x₃ substance from the culture.

In carrying out the process of this invention, any strain of the genus Streptomyces may be used as long as it substantially produces the SF-1130-x₃ substance. A specific Example of the strain which may suitably be used in the present process is the SF-1130 strain which was isolated from a soil sample and which has been designated as *Streptomyces myxogenes* SF-1130 (see "The Research Annual Report of Meiji Confectionery Co.", No. 14, pages 6-9, (1975) or U.S. Pat. No. 4,160,026). This SF-1130 strain has been deposited in a Japanese public depository "Fermantation Research Institute", Japan under deposit number FERM-P. 676 and also in the American Type Collection, Washington D.C., U.S.A., under deposit number ATCC. 31305.

The above-mentioned and further physico-chemical properties of the new compound of this invention are listed below.

(1) Melting point: 183° C. (with decomposition)

(2) Nature: Oligo-saccharide of weakly basic nature (3) Molecular weight: About 830 (as estimated from mass spectrometry analysis of its permethylated derivative)

(4) Elemental analysis: C 43.31%, H 5.88%, N 1.71% and O 49.10% (balance)

(5) Specific optical rotation: $[\alpha]_D^{23} + 154°$ (c 1, in water)

(6) Ultraviolet absorption spectrum: No characteristic absorption peak (in an aqueous solution of 100 μg/ml of the SF-1130-$x_3$ substance).

Infrared absorption spectrum: Shown in FIG. 1 and peaks at 3350 (broad), 1647, 1400 (broad), 1147 and 1033 (broad) cm$^{-1}$.

(7) Proton nuclear magnetic resonance spectrum: Shown in FIG. 2.

(8) Carbon nuclear magnetic resonance spectrum: Shown in FIG. 3.

(9) Solubility in solvent: Soluble in water and dimethylsulfoxide; less soluble in an alcohol such as methanol and ethanol; insoluble in acetone, ethyl acetate, chloroform and benzene

(10) Color reaction: Positive to silver nitratesodium hydroxide, red tetrazolium, anthrone and Greig-Leaback reagents

(11) R$_{raffinose}$ values in paper chromatography: 0.64 in paper chromatography by the descending method with Toyo filter paper No. 50 and developed with ethyl acetate-pyridine-water (10:4:3), and 0.62 in the same paper chromatography by the descending method developed with n-butanol-pyridine-acetic acid-water (6:4:1:3) as assumed that R$_f$ of raffinose is 1.00 in the same paper chromatography.

(12) Acid hydrolyzate: containing a substantial amount of D-glucose.

Referring to the attached drawings.

Figure 1:
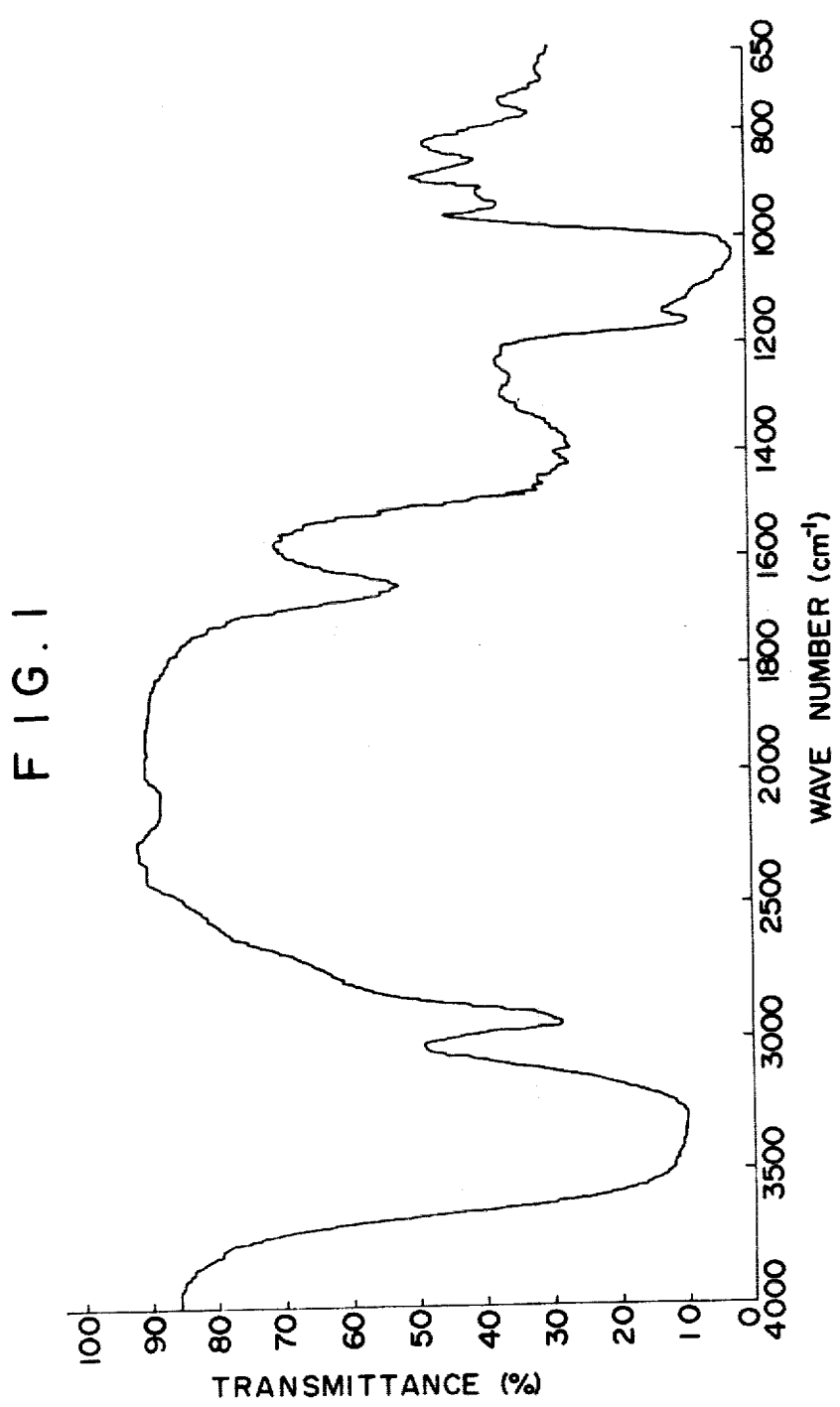
FIG. 1 shows a curve of the infrared absorption spectrum of a pure sample of the SF-1130-$x_3$ substance of this invention pelleted in potassium bromide.

In view of the physico-chemical properties described above, the compound of this invention is compared to known analogous substances. A summary of the results of the comparison is described below.

(1) Japanese Patent Application Pre-publication "Kokai" No. 53593/75 (corresponding to German DT-OS P No. 23 47 782) discloses an amino-sugar of the general formula

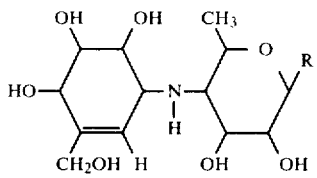

wherein R denotes an oligosaccharide comprising 1 to 7 units of a monosaccharide, which is an inhibitor to amylase. Japanese Patent Application Pre-publication "Kokai" No. 122342/77 (corresponding to German DT-OS P No. 26 14 393) and the "Naturwissenschaften" 64, 535 (1977) disclose an amino-sugar of the general formula

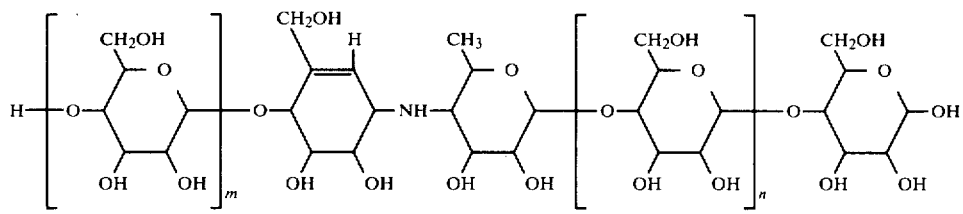

wherein m is an integer of 1-8 and n is zero or an integer of 1-8 but m+n equals to an integer of 3-8, which is an inhibitor to a glucoside-hydrase. Further, Japanese Patent Application Pre-publication "Kokai" No. 92909/79 discloses an amino-sugar of the general formula

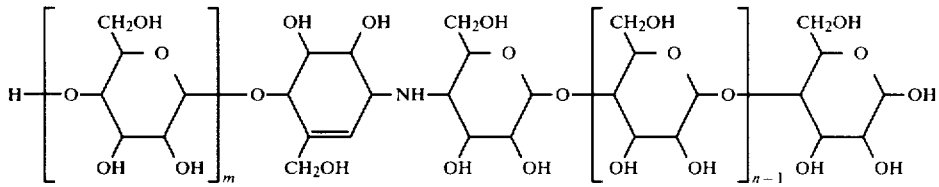

wherein m is zero or an integer of 1-8 and n is an integer of 1-8 but m+n equals to an integer of 1-8, which is also an inhibitor to α-amylase, saccharase, maltase and the like. All of the known amino-sugars of the above-mentioned publications contains the vinyl proton which shows a peak at δ 5.8-6.0 in their proton nuclear magnetic resonance absorption spectra. The new compound of this invention, however, does not show the peak at δ 5.8-6.0 in its proton nuclear magnetic resonance absorption spectrum and hence does not contain the vinyl proton in the molecule thereof.

(2) Japanese Patent Application Pre-publication "Kikai" No. 54990/76 and Japanese Patent Publication No. 24119/77 disclose a glucoamylase-inhibitor which is produced by a microorganism Streptomyces sp. No. 33 (deposited under FERM-P 2788) (identified as a strain of *Streptomyces atroolivaceus*) and which is an acidic substance having no optical activity. In contrast to this glycoamylase-inhibitor, the new compound of this invention is a weakly basic substance having an optical activity.

(3) Japanese Patent Publications No. 21596/77 and No. 21597/77 disclose an amylase-inhibitor which is designated "amylostatin A" and produced by a microorganism *Streptomyces var. amylostaticus* (deposited under FERM-P No. 2499) and which is deemed as a neutral polysaccharide of a molecular weight of about 2000. In these respects, the new compound of this invention is distinguishable from amylostatin A, and besides the new compound of this invention gives a different Rf value from that of amylostatin A in a paper chromatography.

(4) The "J. Jap. Soc. Starch Sci." 26, No. 2, pp. 134–144 (1979) discloses a further amylase-inhibitors TAI-A and -B of *Streptomyces calvus* TM-521 which do not show the signal of methyl group at δ ca. 1.35 in the proton nuclear magnetic resonance absorption spectrum, and in this respect, these amylase-inhibitors are distinctive from the new compound of this invention which gives the signal of methyl group at δ ca. 1.35 in the proton nuclear magnetic resonance spectrum thereof.

(5) Japanese Patent Application Pre-publication "Kokai" No. 26398/78 of the same applicant or the corresponding U.S. Pat. No. 4,160,026 discloses the SF-1130-$x_1$ and SF-1130-$x_2$ substances which are common to the new compound of this invention in that they all are an amino-sugar of a weakly basic nature and gives glucose when hydrolyzed and in that all of them do not show the signal of the vinyl proton in the proton nuclear magnetic resonance spectra of them. However, they are evidently distinguishable from each other in that they have different molecular weights and give different Rf values in a paper chromatography.

Furthermore, our recent structural studies of the SF-1130-$x_1$, SF-1130-$x_2$ and SF-1130-$x_3$ substances have now revealed that these substances may be represented by a general formula tion method in a culture medium containing nutrient sources which are assimilable by ordinary microorganisms. For this purpose, use may be made of any known nutrients which have been generally employed for the cultivation of known strains of the genus Streptomyces. Examples of the nutrient sources include glucose, starch, starch syrup and molasses as the carbon sources; and soybean meal, wheat embryo, dried yeast, peptone, meat extract, corn steep liquor, ammonium sulfate and sodium nitrate as the nitrogen sources. If required, inorganic salts such as calcium carbonate, sodium chloride, potassium chloride, phosphates and the like may be added. In addition, such organic and inorganic materials as aid the growth of the strain used and promote the production of the SF-1130-$x_3$ substance according to this invention may be incorporated in the culture medium.

As the cultivation methods which can be employed in the process of this invention, liquid cultivation, particularly under submerged aerobic conditions, is most prefered as is generally used in the production of known antibiotics. For commercial procedure, the cultivation is advantageously conducted at 25°–38° C., especially at about 28° C. under submerged aerobic conditions using a suitable production culture medium to which has been inoculated a spore suspension of the SF-1130 strain or a seed culture of said strain which was cultivated for 2 to 3 days. As the culture medium and cultivation conditions to be used in the process of this invention, there can be equivalently applied the culture medium and cultivation conditions which are disclosed in our U.S. Pat. No. 4,160,026.

For the recovery of the crude product containing the compound of this invention from the fermantation broth of the SF-1130 strain, there can be equally applied the isolation and concentration procedures which are employed in the recovery of the SF-1130-$x_1$ and SF-1130-$x_2$ substances as described in U.S. Pat. No. B 4,160,026, since the compound of this invention is very similar to the SF-1130-$x_1$ and SF-1130-$x_2$ substance in their nature.

Thus, the fermentation broth containing the SF-1130-$x_3$ substance is filtered under neutral conditions to remove the mycelia and insoluble materials, and then

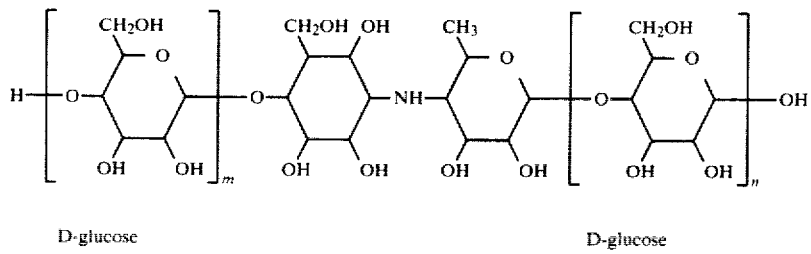

D-glucose                    D-glucose and m+n equals to 5 in respect to the SF-1130-$x_1$ substance; m+n equals to 4 in respect of the SF-1130-$x_2$ substance; and m+n equals to 3 but m=zero, n=3 in respect of the SF-1130-$x_3$ substance. Moreover, the SF-1130-$x_3$ substance of this invention shows a higher activity to an α-glucosidase than the SF-1130-$x_1$ and SF-1130-$x_2$ substances as shown hereinafter.

In account of the above-mentioned comparisons, it is clarified that the compound of this invention is a new one.

In carrying out the process of this invention, the SF-1130 strain as mentioned above may be cultivated either by liquid cultivation method or by solid cultivathe broth filtrate at neutral pH value is treated with active carbon for adsorption of the active substances. The carbon is then extracted with 50 to 60% acetone-water to desorb the SF-1130-$x_3$ substance from the active carbon. The extract is concentrated to dryness, the residue is dissolved in water and the aqueous solution at a weakly acidic pH value is subjected to a chromatography on a strongly acidic ionexchange resin such as Dowex 50 W×2 (H+ form), followed by washing with water and eluting with 0.1 N aqueous ammonia. The eluate is collected in fractions, and the antibacterially active fractions are combined together and concentrated to dryness to give a crude product comprising the compound of this invention in the form of a colorless powder.

For the separation of the compound of this invention from the SF-1130-$x_1$ and SF-1130-$x_2$ substances, this crude powder is taken up into water and adjusted to pH 2 by 0.5 N HCl, and the resulting aqueous solution is subjected to a chromatography on a strongly acidic cation-exchange resin such as Dowex 50 W$\times$2 (pyridinium salt form) developed with 0.1 M pyridine-formic acid buffer (pH 3.1) as the development solvent. The SF-1130-$x_1$ and SF-1130-$x_2$ substances are firstly eluted out of the resin column. Upon further elution with the same development solvent as above, the SF-1130-$x_3$ substance appears in the further eluate which is collected in fractions, and those fractions containing solely the SF-1130-$x_3$ substances are combined together and concentrated to dryness to afford the compound of this invention as a colorless pure powder. By taking advantage of the fact that the molecular weight of the compound of this invention is lower than those of the SF-1130-$x_1$ and SF-1130-$x_2$ substances, the compound of this invention can also be separated from the SF-1130-$x_1$ and -$x_2$ substances by utilizing the conventional isolation technique such as gel-filtration procedure, for example with aid of Biogel p-2, Sephadex G-10 (Pharmacia Co., Sweden) and the like as the gel-filtration agent.

The compound of this invention is useful for highly inhibiting the enzymatic reaction of glucosidase and particularly for inhibiting the enzymatic reaction of $\alpha$-glucosidase as well as the enzymatic reaction of saccharase. Such inhibitory activity of the compound of this invention may be estimated according to the following procedure with the $\alpha$-glucosidase prepared from ileum mucosa of pig as disclosed in the literature "Acta Chem. Scand." vol. 12, page 1997 (1958).

(1) Determination of the activity of inhibiting $\alpha$-glucosidase. There are prepared the following four solutions:

Solution A: A solution of the enzyme ($\alpha$-glucosidase) having appropriately been diluted to a desired enzyme concentration with 0.1 M maleate buffered solution (pH 6.0)

Solution B: 0.1 M maleate buffered solution (pH 6.0)

Solution C: An aqueous solution of 0.014 M p-nitrophenyl-$\alpha$-D-glycoside (as the substrate) in water Solution D: An aqueous solution of 0.1 M sodium carbonate in water 0.5 ml of a solution which was obtained by dissolving a sample of the enzyme-inhibitor to be assayed to an appropriate concentration in said Solution B is placed together with 0.25 ml of Solution C into a test tube, and this test tube is immersed at 37° C. for 5 minutes in a water bath maintained at the same temperature. The mixed solution in said test tube is further admixed with 0.25 ml of Solution A to start the enzymatic reaction. 20 Minutes after the start of the reaction, 5 ml of Solution D is added to the reaction solution to cease the enzymatic reaction. Absorbancy at 400 nm of the resulting reaction solution is measured, and the found value of the absorbancy is denoted as T. Further, the above-mentioned operation is repeated (as a blank-test) without use of the sample of the enzyme-inhibitor and then the absorbancy at 400 nm of the control reaction solution obtained from this blank test using Solution B, ie., the 0.1 M maleate buffered solution containing no enzyme-inhibitor is measured in the same way as above, and the found value of the absorbancy is denoted as C.

In the above assay, degree (%) of inhibition for the inhibitor sample to the $\alpha$-glucosidase is calculated according to the following equation:

$$\text{Inhibition (\%)} = (C-T)/C \times 100$$

(2) Determination of the activity of inhibiting saccharase.

There are prepared the following three solutions:

Solution A: A solution of a saccharase having been diluted to an appropriate enzyme concentration with 0.1 M maleate buffered solution (pH 6.0)

Solution B: 0.1 M maleate buffered solution (pH 6.0)

Solution C: An aqueous solution of 4% sucrose (as the substrate) in water 1.0 ml of a solution which was obtained by dissolving a sample of the enzyme-inhibitor to be assayed to an appropriate concentration in said Solution B is placed together with 0.5 ml of Solution C into a test tube and this test tube is immersed at 30° C. for 5 minutes in a water bath maintained at the same temperature. The resultant mixed solution in said test tube is further admixed with 0.5 ml of Solution A to start the enzymatic reaction. 10 minutes after the start of the reaction, a portion (30 $\mu$l) of the reaction solution is withdrawn and the reducing power of the reaction solution is determined colorimetrically according to the Somogyi-Nelson method. The found value of the absorbancy at 660 nm of said reaction solution is denoted as T.

While, the above-mentioned operation is repeated without the sample of the enzyme-inhibitor and then the absorbancy at 660 nm of the control reaction solution is measured again in the same way as above. The found value of the absorbancy for the control is denoted as C.

In the above assay method, degree (%) of inhibition for the inhibitor sample to saccharase is calculated according to the following equation:

$$\text{Inhibition (\%)} = (C-T)/C \times 100$$

In the above assay, the SF-1130-$x_3$ substance of this invention showed a potency that its ID$_{50}$ (ie. dose of giving 50% inhibition) to $\alpha$-glucosidase was $2.24 \times 10^{-5}$ M and its ID$_{50}$ to saccharase was $2.0 \times 10^{-5}$ M. For comparison, the inhibitory potency of the SF-1130-$x_1$ and SF-1130-$x_2$ substance as well as nojirimycin (known as an amylaseinhibitor) were measured in the same way as above, and the ID$_{50}$ values of the SF-1130-$x_1$ substance, the SF-1130-$x_2$ substance and nojirimycin were estimated to be $1.5 \times 10^{-4}$ M, $1.8 \times 10^{-4}$ M, and $3.6 \times 10^{-4}$ M, respectively.

Besides, it is noteworthy that the compound of this invention is orally given to living animals to exhibit an activity for suppressing an elevation in the level of blood sugar in living animals which have taken starch and sugars orally. The test was carried out by the following procedure: Test animal was ICR-strain male mice (six mice per group, weighing 25 g in average) which had been abstained from water for 20 hours. 1 g/kg of starch or 2.5 g/kg of sucrose was orally given to the mice. At the same time, 10 mg/kg of the compound of this invention or 10 mg/kg of deoxynojirimycin as a comparative drug was orally administered to these mice. 30 minutes after the administration, the glucose level in blood was measured. The test results are shown in Table below.

| Test-drug | Blood sugar level (mg/dl) | |
|---|---|---|
| | Groups receiving starch | Groups receiving sucrose |
| Untreated | 153 ± 24.2 | 189 ± 41.5 |
| Compound of this invention | 88 ± 20.7 | 96 ± 10.2 |
| SF-1130-x$_1$ + -x$_2$ (2:3) | 124 ± 17.8 | 100 ± 20.7 |
| Deoxynojirimycin (Comparative) | 101 ± 22.9 | 93 ± 15.4 |
| Control (receiving neither the starch or sucrose nor the test drug) | 75 ± 11.0 | 66 ± 13.0 |

The antibacterial activity of the SF 1130-x$_3$ substance of this invention to inhibit the growth of various bacteria was estimated according to a conventional paper disc plate method. Thus, the SF-1130-x$_3$ substance was dissolved in distilled water at a concentration of 1 mg/ml. With the test solution so prepared was impregnated a paper disc of filter paper which was subsequently air-dried. It has been found that the compound of this invention at a level of 1 mg/ml gives the inhibition zones of 13.3 mm in diameter against the test microorganism, *Escherichia coli* K-12R.

To estimate acute toxicity of the SF-1130-x$_3$ substance of this invention, this compound was administered orally to five mice; all mice tested tolerated doses of 500 mg/kg of the SF-1130-x$_3$ substance. From the results of this test for acute toxicity, it is clear that the compound of this invention is of very low toxicity.

As will be clear from the above, the new compound of this invention exhibits a remarkably high activity to inhibit glucosidase not only in vitro but also in vivo.

According to a further aspect of this invention, therefore, there is provided an inhibitor to glucosidase which comprises as the active ingredient the SF-1130-x$_3$ substance, optionally in association with a known pharmaceutically acceptable carrier or diluent for the active ingredient.

The inhibitor to glucosidase according to this invention is useful for controlling metabolism of carbohydrates in living animals, including men, for example, in therapeutic treatment of diabetes, obesity, gastritis, gastric ulcer, duodenal ulcer, constipation and the like, as well as for treating secondary diseases which are attributable to the abnormal metabolism of carbohydrates as mentioned above. The glucosidase-inhibitor according to this invention is also useful for preventing dental caries. Carbohydrates, especially sucrose are degraded by the glucosidase of certain microorganism existing in the mouth and the degradation products such as glucose promote the formation of dental caries. However, the degradation of carbohydrates on the surface of the teeth can be suppressed by providing the presence of the glucosidase-inhibitor of this invention in the mouth.

The glucosidase-inhibitor of this invention may be formulated as a solid or liquid preparation containing the SF-1130-x$_3$ substance as active ingredient in association with a solid or liquid carrier or diluent.

The solid preparation may be used in the form of tablets, dragees, capsules or suppository, and the liquid preparation may be used in the form of a gel, cream, suspension, emulsion, syrup or isotonic solution. The solid preparation may contain additionally conventional filler, extender, binder, lubricant and the like. When the inhibitor according to this invention is formulated into a suppository, use may be made of a base such as cocoa butter and the like. The liquid preparation may contain a pharmaceutically acceptable surface-active agent, preservative, flavors, sweetenings and the like, in addition to the conventional diluent such as water, ethyl alcohol, propylene glycol, animal or vegetable oil and the like.

The dosage of the SF-1130-x$_3$ substance of this invention varies depending on the method of administration employed, the nature of diseases, the conditions of a patient suffering from the disease and other conditions. In general, however, the SF-1130-x$_3$ substance of this invention may suitably be given orally at a dose of 100 mg/kg to 1 g/kg per day. When the SF-1130-x$_3$ substance of this invention is administered parenterally, it may be given at a dose of $\frac{1}{2}$ to 1/5 of 100 to 1000 mg/kg.

The SF-1130-x$_3$ substance of this invention may be used not only for the above-mentioned therapeutical purpose but also for prophylactic purpose. For the prophylactic purpose, the SF-1130-x$_3$ substance is incorporated into foods or drinks containing high-calorie carbohydrates, for example, chocolate, bread, jam or soft drink e.g. fruit juice in order to prevent weight-gaining of men who take such foods or drinks. Furthermore, the inhibitor of this invention may be effectively admixed with chewing gum or tooth paste for prophylactic treatment of dental caries.

Further, the SF-1130-x$_3$ substance of this invention may be incorporated into a feedstock for domestic animals to suppress the metabolic conversion of carbohydrates into fat occurring in the animal body and thereby to increase the portion of low-fat meat in the animal body. The SF-1130-x$_3$ substance of this invention may be added to the feedstuff in an amount of 10–100 mg per kg of the feedstuff.

The SF-1130-x$_3$ substance of this invention is also useful as an amylase-inhibitor which is frequently used in bio-chemical analysis for medical examination or for laboratory researches.

It is known that when the carbohydrates such as starch and sugars are taken by living animals, including men, they are converted into glucose under the action of the glucosidase in the digestive tubes of the animals and then absorbed into the blood. When an excessive amount of glucose is absorbed into the blood of living animals, it brings about a too much gain in the body weight of the animals which occasionally incurs unhealthy results. When a patient suffering from diabetic has taken much carbohydrates, the glucose level in the blood can elevate abnormally too much and bring about undesirable effects in the conditions of the patient. Accordingly, it is useful if the metabolic conversion of the carbohydrates into glucose by the glucosidase in the digestive tubes of a human is suppressed. According to a further aspect of this invention, therefore, there is provided a method of suppressing the enzymatic activity of glucosidase in the digestive tubes of living animals, including men, which comprises administering orally an effective amount of the SF-1130-x$_3$ substance of this invention to the animals.

This invention is now illustrated with reference to the following Examples to which this invention is not limited.

EXAMPLE 1

A seed culture of *Streptomyces myxogenes* SF-1130 strain (identified as FERM-P. 676 or ATCC. 31305) was inoculated to 200 l of a liquid culture medium comprising 5.0% starch syrup, 2.5% soybean meal, 1.0% wheat embryo and 0.25% sodium chloride. The inoculated medium was incubated in a jar-fermentor under aeration and agitation at 28° C. for 64 hours.

At the end of the incubation, 50 l of the resultant culture broth were adjusted to pH 2.0 by addition of 5 N nitric acid, admixed with 50 g of active carbon and 2 kg of a filtration-aid and the admixture was agitated for 15 minutes and then filtered. The resultant filtrate was neutralized with aqueous ammonium hydroxide and admixed with 1 kg of active carbon for the adsorption of the active substance, followed by stirring for 30 minutes. The stirred admixture was filtered and the active carbon removed was washed with three 10 l portions of distilled water. Subsequently, the active carbon was extracted for 15 minutes with 4 l of an aqueous solution of 60% acetone at pH 2.5 under stirring to desorb the active substance out of said active carbon. This extraction procedure was repeated twice, and the resultant extracts were combined together and concentrated to a small volume. The concentrated solution was added dropwise into 5 l of acetone to deposit 90 g of a colorless precipitate.

The colorless precipitate was collected by filtration and taken up into 250 ml of distilled water, and the resultant solution was passed through a column (4×40 cm) of a strongly acidic cation-exchange resin, Amberlite IR-120 ($H^+$ form) (a product of Rohm & Hass Co.) for the adsorption of the active substance on the resin. After thorough washing with distilled water, the resin column was eluted with 2% aqueous ammonium hydroxide. The eluate was collected in 20 ml-fractions, and such fractions active against *E. coli* K-12R were combined together and concentrated to dryness under reduced pressure to give 5.0 g of a brown colored powder.

This powder (5.0 g) was then taken up into 50 ml of distilled water and the solution obtained was passed through a column (3×70 cm) of Dowex 50 W×2 (pyridinium form 200-400 mesh) (a product of Dow Chemical Co., U.S.A.) for the adsorption of the active substance. The resin column was then eluted with a buffer solution of 0.1 M pyridine-formic acid (pH 3.1). The eluate was collected in 10 ml-fractions, and the active fractions Nos. 101-120 containing the SF-1130-$x_1$ substance and the active fractions Nos. 130-170 containing the SF-1130-$x_2$ substance were obtained. The resin column was further eluted with the same buffer solution as above to give the active fractions Nos. 180-224 containing solely the SF-1130-$x_3$ substance of this invention which gave a single spot (colored by the silver nitrate-sodium hydroxide reagent) at an $R_{raffinose}$ value of 0.64 in a paper chromatography by the descending method developed with ethyl acetate-pyridine-water (10:4:3) as the developing solvent. The active fractions Nos. 180-224 which showed the same $R_{raffinose}$ value as above were combined together and concentrated to dryness to afford about 800 mg of a colorless powder.

This colorless powder was dissolved in 2 ml of distilled water and the resultant aqueous solution was passed through a column of 100 ml of a gel-filtration agent, Biogel p-2 (a product of Bio Rado Co.) developed with water as the development solvent. The eluate was collected in 8 ml-fractions, and the antibacterially active fractions Nos. 35-43 were combined together and concentrated to dryness to give about 400 mg of a pure product of the SF-1130-$x_3$ substance as a colorless powder. m.p. 183° C. (dec.). $[\alpha]_D^{23} + 154°$ (c 1, water).

The following Examples 2 and 3 illustrate the preparation of chocolate or juice into which the SF-1130-$x_3$ substance of this invention is incorporated as the glucosidase-inhibitor.

EXAMPLE 2

The ingredients mentioned below were formulated into chocolate by mixing them together in a mixer in proportions indicated below.

| Ingredient | % by weight |
| --- | --- |
| SF-1130-$x_3$ substance | 0.1 |
| Bitter | 15.85 |
| Oleo-butter | 5.0 |
| Sugar | 44.0 |
| Vanillin | 0.05 |
| Lecithin | 0.6 |
| Cocoa milk | 23.0 |
| Cocoa butter | 11.4 |
| Total | 100.00 |

EXAMPLE 3

The ingredients mentioned below were formulated into juice drink by mixing them together in a mixer in proportions indicated below.

| Ingredient | % by weight |
| --- | --- |
| SF-1130-$x_3$ substance | 0.05 |
| Isomerized sugar | 13.5 |
| Citric acid | 0.17 |
| Sodium citrate | 0.016 |
| Lemon flavor | 0.1 |
| Water | 86.164 |
| Total | 100.0 |

Figure 2:
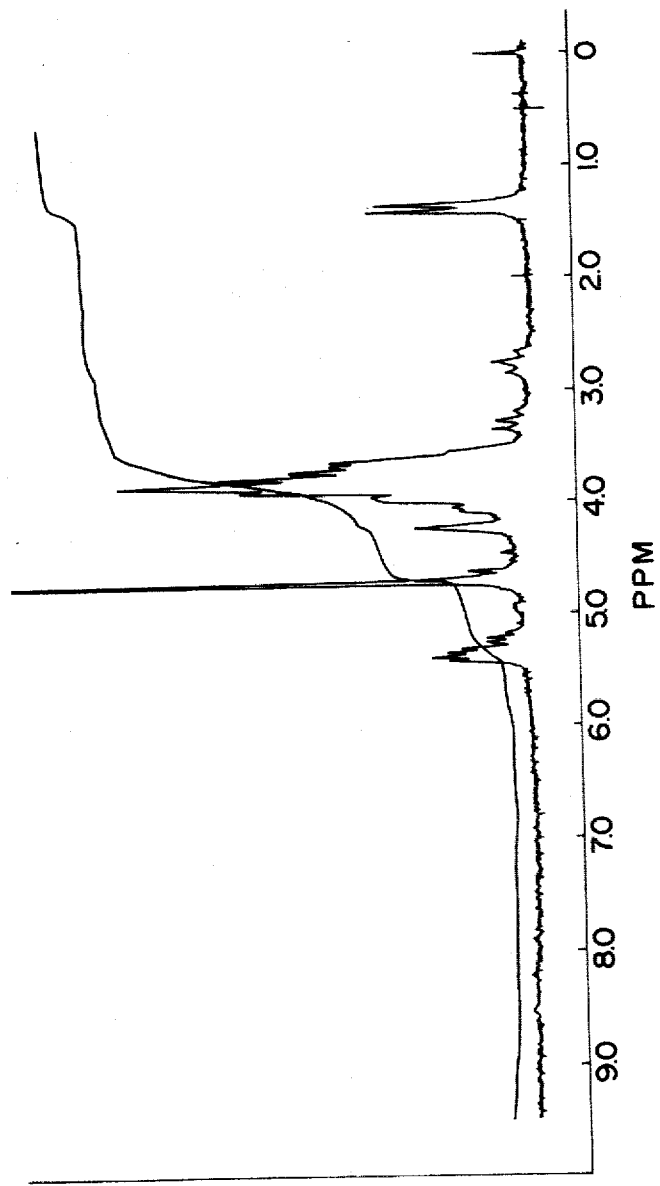
FIG. 2 shows a curve of the proton nuclear magnetic resonance absorption spectrum of a pure sample of the SF-1130-$x_3$ substance determined in deuterium oxide at 100 MHz.
Figure 3:
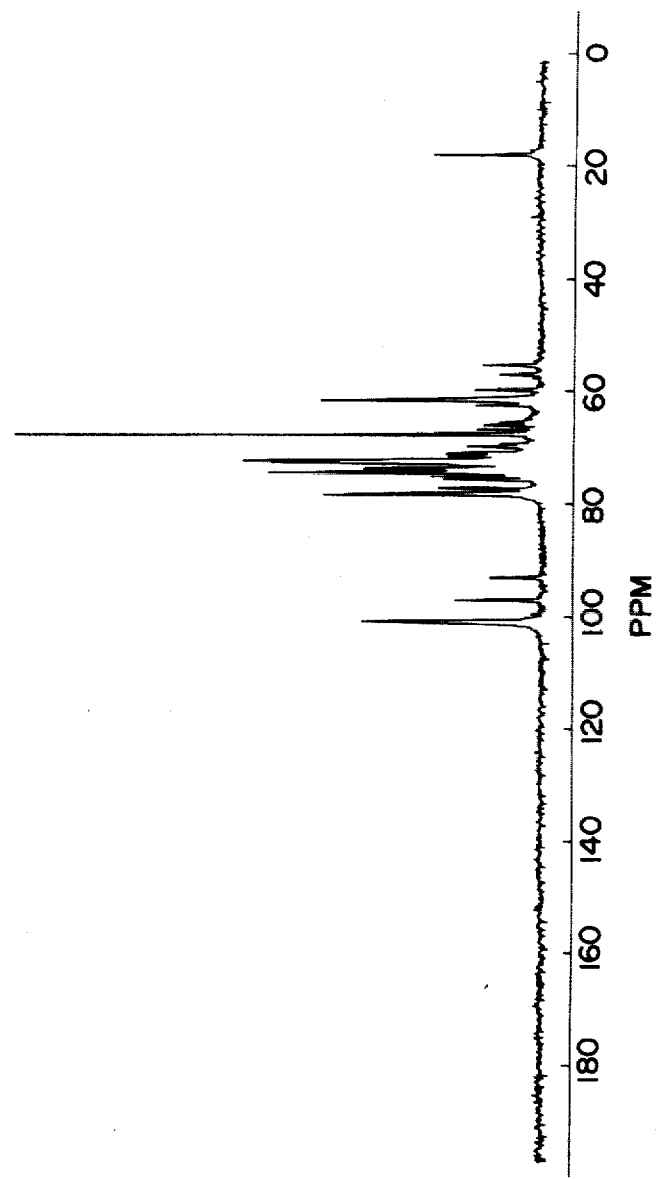
FIG. 3 shows a curve of the carbon nuclear magnetic resonance absorption spectrum of a pure sample of the SF-1130-$x_3$ substance determined in deuterium oxide at 100 MHz.

What we claim is:

1. The SF-1130-$x_3$ substance which is an oligosaccharide of weakly basic nature in the form of a colorless powder, which is soluble in water and dimethylsulfoxide, less soluble in methanol and ethanol but insoluble in acetone, ethyl acetate, chloroform and benzene and which shows positive reaction with silver nitrate-sodium hydroxide, red tetrazolium, anthrone and Greig-Leaback reagents, respectively; the SF-1130-$x_3$ substance being further characterized by:
   (a) having a melting point of 183° C. (with decomposition) and a specific optical rotation $[\alpha]_D^{23} + 154°$ (c 1, in water);
   (b) exhibiting an elemental analysis: C 43.31%, H 5.88%, N 1.71% and O 49.10% (balance);
   (c) having no characteristic absorption peak in ultraviolet spectrum (in water containing 100 μg/ml of a pure sample of the SF-1130-$x_3$ substance);
   (d) having an infrared absorption spectrum pelleted in potassium bromide corresponding to that shown in FIG. 1 of the attached drawings;
   (e) having a proton nuclear magnetic resonance absorption spectrum in deuterium oxide corresponding to that shown in FIG. 2 of the attached drawings;
   (f) having a carbon nuclear magnetic resonance absorption spectrum in deuterium oxide corresponding to that shown in FIG. 3 of the attached drawings; and
   (g) giving a single spot at $R_{raffinose} = 0.64$ in a paper chromatography by the descending method developed with ethyl acetate-pyridine-water (10:4:3) as the developing solvent and at $R_{raffinose}=0.62$ in the same paper chromatography by the descending method developed with n-butanol-pyridine-acetic acid-water (6:4:1:3) as the developing solvent when the $R_{raffinose}$ values are calculated as assumed that raffinose gives a single spot at $Rf=1.00$ in the same paper chromatography.

2. An inhibitor to glucosidase, which comprises as the active ingredient the SF-1130-$x_3$ substance as defined in claim 1, in an amount effective to inhibit the enzymatic activity of glucosidase, in combination with a pharmaceutically acceptable carrier for the active ingredient.

3. The method of suppressing the enzymatic activity of glucosidase in the digestive tubes of living animals, which comprises administering orally to said animal an amount of the SF-1130-$x_3$ substance as defined in claim 1 effective to inhibit the enzymatic activity of glucosidase.

* * * * *